United States Patent [19]

Schultz et al.

[11] Patent Number: 4,808,576
[45] Date of Patent: Feb. 28, 1989

[54] REMOTE ADMINISTRATION OF HYALURONIC ACID TO MAMMALS

[75] Inventors: Richard H. Schultz, Lenexa; Terry H. Wollen, Wellsville; Nathan D. Greene, Leawood, all of Kans.; Karen K. Brown, Kansas City, Mo.; John O. Mozier, Stanley, Kans.

[73] Assignee: Mobay Corporation, Pittsburgh, Pa.

[21] Appl. No.: 856,732

[22] Filed: Apr. 28, 1986

[51] Int. Cl.$^4$ ............................................ A61K 31/715
[52] U.S. Cl. ............................................ 514/54; 514/825; 536/55.1
[58] Field of Search ............... 514/54, 825; 536/55.1

[56] References Cited

U.S. PATENT DOCUMENTS

| | | | |
|---|---|---|---|
| 4,055,660 | 10/1977 | Meierhenry | 514/537 |
| 4,141,973 | 2/1979 | Balazs | 536/55.1 |
| 4,272,522 | 6/1981 | Balazs | 424/94.61 |
| 4,296,104 | 10/1981 | Herschler | 424/153 |
| 4,427,649 | 1/1984 | Dingle et al. | 514/179 |
| 4,517,295 | 5/1985 | Bracke et al. | 536/55.1 |
| 4,521,406 | 6/1985 | Kawamura et al. | 424/94.61 |

FOREIGN PATENT DOCUMENTS

| | | |
|---|---|---|
| 0143393 | 6/1985 | European Pat. Off. |
| 8605984 | 10/1986 | World Int. Prop. O. |

OTHER PUBLICATIONS

Chemical Abstracts, Band 102, Nr.11, Mar. 18, 1985, Nr. 89817, Columbus, Ohio, "Studies on Analgesic and Anti-Inflammatory Effects of Sodium Hyaluronate".

Chemical Abstracts, Band 106, Nr.7, Feb. 16, 1987, Nr. 43520u, Columbus, Ohio, "Topical Treatment of Experimental Skin Lesions in Rats".

Preliminary Clinical Assessment of NaHyaluronate Injection Into Human Arthritic Joints, by Peyron et al, vol. 22, No. 8, pp. 731–736, Oct., 1974.

Decreased Granulation Tissue Reaction After Installment of Hyaluronic Acid, by Rydell, pp. 307–311, vol. 41, of Acta Orthop Scandinav.

Letter in Veterinary Medicine, pp. 446–447, Apr. 1984 Issue.

Influence of a Glycosaminoglycan Polysulfate on Iysosomal Enzyme Release from Human Polymorphonuclear Leukocytes, vol. 41, pp. 50–53, 1982.

Polysulfated Glycosaminoglycan: A New Intra-Articular Treatment for Equine Lameness, Vet. Medicine, pp. 811–816, Jun. 1984.

Clinical Orthopaedics, pp. 25–32, Oct., 1971, No. 80, by Rydel et al, "Effect of Intra-Articular Injection of Hyaluronic Acid on Clinical Symptoms".

Influences of Sulfated Glycosaminoglycans on Biosynthesis of Hyaluronic Acid in Rabbit Knee Synovial Membrane, by Nishikawa, pp. 146–153, Jul. 1985, vo. 240.

Vergleich von Glykosaminoglykanpolysulfat und Physiologischer Kochsalzlosung bei Arthorosen Grober Gelenke, pp. 223–228, vol. 42, Jul. 1983.

Die Tierexperimentelle Gonartrose der Ratte und Ihre Therapie mit Glykoaminoglykan Polysulfat, pp. 100–107, vol. 44, 1985.

*Primary Examiner*—Ronald W. Griffin
*Attorney, Agent, or Firm*—Gene Harsh; Joseph C. Gil; Lyndanne M. Whalen

[57] ABSTRACT

The present disclosure is concerned with the discovery that hyaluronic acid, an agent well known to reduce the sequelae of trauma in mammalian joint tissue when applied directly to the traumatized tissue, will be carried to such traumatized tissue by the mammal's natural processes if applied at a site remote from the traumatized tissue. Thus, hyaluronic acid, in any therapeutically acceptable form, can be administered by the typical remote routes including intravenous, intramuscular, subcutaneous and topical.

This makes the utilization of hyaluronic acid much more convenient and attractive. For instance the treatment of arthritis in horse or human joints with hyaluronic acid no longer requires more difficult intra articular injections.

35 Claims, 6 Drawing Sheets

REMOTE ADMINISTRATION OF HYALURONIC ACID TO MAMMALS

FIELD OF THE INVENTION

The present invention is concerned with the discovery that a known therapeutic agent, hyaluronic acid, can be effectively administered to mammals by techniques which require the mammal's internal bodily processes to transport this high molecular weight agent to the site of action.

BACKGROUND OF THE INVENTION

Hyaluronic acid is a well known mucopolysaccharide which is found in the joint tissue and vitreous humor of the eyes of mammals. It has been extracted from rooster combs and human umbilical cords and bacterial cultures such as those of hemolytic group A and C streptococci for various therapeutic purposes. The initial therapeutic use of this material was as a replacement for the liquid vitreous of the human eye to aid in ophthalmic surgery, especially in the treatment of retinal detachment. It has also found utility for the relief of trauma or irritation in joint tissue of mammals including humans by injection into the synovial fluid of the joint. It has been proposed that it be used both as a primary medicant and as an auxiliary with other joint medicines. An extensive discussion of its various utilities is found in U.S. Pat. No. 4,141,973 to Balazs. The use of hyaluronic acid alone and with cortisone in various animal joints, especially horses, is discussed in the "Effect of Intra-articular Injection of Hyaluronic Acid on the Clinical Symptoms of Osteoarthritis and on Granulation Tissue Formation" by Rydell et al. and appearing at pages 25 to 32 of the October, 1971 (Number 80) issue of *Clinical Orthopaedics and Related Research*. The use of hyaluronic acid in human joints is reported in the "Preliminary Clinical Assessment of Na Hyaluronate Injection into Human Arthritic Joints" by Peyron et al and appearing at pages 731 to 736 of the October 1974 (Volume 22, Number 8) of *Pathologie Biologie*. Finally, the use of hyaluronic acid in reducing fibrotic wound reactions is reported in the "Decreased Granulation Tissue Reaction After Installment of Hyaluronic Acid" by Rydell and appearing at pages 307 to 311 of Volume 41 of *Acta Orthop. Scandinav.*

The intra-articular use of hyaluronic acid in horse joints has been commercially promoted in connection with Pharmacia's Hylartil and Hylartin V product and Sterivet's Synacid product. However, the commercial attractiveness has been limited by the need to administer these products by injection into the affected joint.

A related material, a polysulfated glycosaminoglycan, has recently been introduced to the U.S. market by Luitpold Pharmaceuticals under the tradename Adequan ® (also known in Europe as Arteparon) for the treatment of arthritic joints in horses. Initially the recommended route of administration was intra-articular with a 250 mg injection each week for five weeks. A letter appearing at pages 446 and 447 of the April 1984 issue of *Veterinary Medicine* suggests that this material can be administered intramuscularly at approximately double the dosage on a four day interval for four to five weeks.

Polysulfated glycoaminoglycans have also been reported to stimulate the biosynthesis of hyaluronic acid in the synovial membranes of rabbit knee joints thus suggesting that although the mode of action may be different from hyaluronic acid the same conditions might be beneficially effected. Interestingly the report, "Influences of Sulfated Glycosaminoglycans on Biosynthesis of Hyaluronic Acid in Rabbit Knee Synovial Membrane", by Nishikawa et al and appearing at pages 146 to 153 of the July, 1985 issue (Volume 240) of *Arch. Biochem. Biophys.* indicates that hyaluronic acid itself has no such stimulatory effect.

This stimulatory agent has been reported to be effective if administered either intramuscularly to humans or subcutaneously to rats. The former effect is noted in "Vergleich von Glykosaminoglykanpolysulfat (Arteparon) und physiologischen Kochsalzloesung bei Arthrosen grosser Gelenke.Ergebnisse einer multizentrischen Duppelbindstudie" by Siegmeth et al and appearing at pages 223 to 228 of the July/August 1983 issue (Volume 42, Number 4) of *Z. Rheumatol*. The latter effect is discussed in "Die Tierexperimentelle Gonarthrose Der Ratte und Ihre Therapie mit Glyko-aminoglykan polysulfat" by Buchmann et al and appearing at pages 100 to 107 of the 1985 issue (Volume 44, Number 3) of *Z. Rheumatol.*

This stimulatory agent has also been reported to have a broad range of lower molecular weights. In the "Influence of a Glycosaminoglycan Polysulfate (Arteparon) on Lysosomal Enzyme Release from Human Polymorphonuclear Leukocytes" by Mikulikova and appearing at pages 50 to 53 of the March/April 1982 issue (Volume 41, Number 2) of *Z. Rheumatol* is an indication that Arteparon can be fractionated into portions having molecular weights between 3000 and 17,000. In "Polysulfated Glycosaminoglycan: a New Intra-articular Treatment for Equine Lameness" by Hamm, Goldman and Jones appearing at pages 811 to 816 of the June, 1984 issue of *Veterinary Medicine* Adequan is reported to have an approximate molecular weight of 10,000. In this regard, one of the coauthors, Dr. Goldman, is associated with Lutipold Pharmaceuticals, the U.S. distributor of this product.

The direct use of hyaluronic acid has been found to be effective at lower dosages than this polysulfated glycosaminoglycan, which stimulates hyaluronic acid production in joint tissue. For instance the Adequan polysulfated glycosaminoglycan is sold with a dosage recommendation of 250 mg for intra-articular administration to horses whereas Pharmacia markets hyaluronic acid under the name Hylartil with a recommended dosage for intraarticular administration of 20 mg. Although the Adequan product has been reported to be effective when administered intramuscularly at double the dose (500 mg) a similar effect was not expected for the high molecular weight sodium hyaluronate.

It was not expected that sodium hyaluronate would be amenable to remote administration because its primary action was thought to be lubrication and because of its molecular weight which is typically well in excess of $1 \times 10^6$ daltons. It was expected that molecules of such a molecular weight would be too large to transfer through mammalian tissue to the remote site of trauma. Thus, it was assumed that effective amounts of sodium hyaluronate could not be transported through the body of a mammal to the site of action upon the remote administration of reasonable sized doses.

It has now been found that the remote administration of hyaluronic acid is effective in reducing the pain and swelling of traumatized or irritated mammalian tissue, particularly joint tissue.

SUMMARY OF THE INVENTION

A process for reducing the sequela of the trauma in irritated or inflamed mammalian tissue by the remote administration of hyaluronic acid or a pharmacologically acceptable salt thereof has been discovered. (Hereinafter for convenience the term hyaluronic acid is used to denote both the free acid and the pharmacologically acceptable salts thereof interchangeably except where otherwise explicitly indicated). The hyaluronic acid is introduced to the body of the mammal at other than the site of the traumatized tissue and is effectively transported to the site of action by the body's internal processes. This allows the use of such convenient routes of administration as intramuscular, intravenous, subcutaneous, and topical. Two particularly preferred routes of administration are intramuscular injection and topical application in a recognized transdermal carrier and a particularly amenable condition for such treatment is irritated or inflamed joint tissue.

DETAILED DESCRIPTION OF THE INVENTION

The trauma in irritated or inflamed mammalian tissue is reduced by applying hyaluronic acid by any of the accepted routes of administration except direct application to the affected tissue. A particularly interesting embodiment involves the treatment of joint tissue. The direct application of hyaluronic acid involves intra-articular injection which is a procedure requiring considerable care and skill in the larger joints of larger mammals such as the leg joints of horses. The treatment of smaller mammals such as dogs and cats and the smaller joints of larger mammals such as human finger joints requires correspondingly greater care and skill. Treatment by remote administration such as intramuscular, intravenous or subcutaneous injection or topical application in a transdermal carrier in such cases is much more convenient and attractive. However, the fact that the internal transport systems of the mammalian body are effective in conveying hyaluronic acid to the affected site makes it possible to treat other traumatized tissue by remote application as well. Thus, remote administration can be used to treat the other conditions for which hyaluronic acid has found utility such as the post surgical adhesions associated with incisions and tendon repair reported on in the Rydell et al article appearing at pages 25 to 32 of the October 1971 issue of *Clinical Orthopedics and Related Research.*

The hyaluronic acid useful in the treatment of irritated or inflamed tissue by remote application may be of any type already recognized as useful for such purposes. It may be extracted from animal tissue such as rooster combs or umbilical cords or from bacterial cultures such as those of hemolytic group A or C streptococci. It should be pure enough to avoid provoking an adverse or toxic reaction in the mammal being treated. This implies that it is free of pyrogens and has a sufficiently low level of proteins and nucleic acids that no substantial immune reaction is provoked. It is preferably of high molecular weight and is also preferably of low viscosity for the injection routes. The polymer may be in its free acid form or in any pharmacologically acceptable salt form.

The preferred source of hyaluronic acid is a culture of an appropriate microorganism. The use of the culturing and harvesting techniques described in European Published Patent Application No. 144,019 are particularly valuable in obtaining material with desirable purity and molecular weight. Among the organisms to which these techniques can be applied the Group A and Group C streptococci are preferred with the Group C being especially preferred and the *Streptococcus equi* being most preferred. Further preferred is the hyaluronic acid obtained according to the teachings of copending U.S. patent application Ser. No. 816,548 filed Jan. 6, 1986.

Both the protein and amino acid content, and the nucleic acid content of the hyaluronic acid should be carefully controlled because both are known to display antigenic activity in mammals. The content of both are conveniently monitored and evaluated by UV absorbance with the former correlated to the optical density at 280 nanometers and the latter to the optical density at 257 nanometers. It is preferred that the content of the former be less than about 1.25, especially less than about 0.1, mg/ml and that the content of the latter be less than about 0.06, especially less than about 0.005, mg/ml. In this regard the absorbance at 280 nanometers does not distinguish between amino acids and proteins. However, while amino acids alone are non-antigenic, they readily complex with hyaluronic acid and the complex may readily provoke an immune response in mammals. Therefore in the context of the present technology it is desirable to control the content of both and thus it is appropriate to specify a maximum content for the combination of both which is correlated with a particular UV absorbance. In an especially preferred hyaluronic acid the total amino acid content as measured by the orthophthalaldehyde fluoresence technique (which inherently involves the hydrolysis of any protein present back to its constituent amino acids) is less than about 0.4 mg/ml and the nucleic acid content is less than about 0.06 mg/ml as measured by the ethidium bromide fluorescence technique.

The hyaluronic acid can be utilized in its free acid form or in any pharmacologically acceptable salt form. One of the most convenient forms is as the sodium salt because this polymer is typically purified by successive precipitations in ethanol or other organic solvents and dissolutions in water and the sodium salt is particularly amenable to such procedures. In fact, all the limitations on purity, viscosity and molecular weight discussed herein were developed on the sodium salt as were the specific application data discussed hereinafter. However, the remote application development is equally applicable to other forms such as the free acid or potassium salt. For convenience the discussion herein includes all these forms within the term hyaluronic acid.

The hyaluronic acid should have a high average molecular weight. Although forms of this material with average molecular weights of 55,000 or less are known the preferred hyaluronic acid has an average molecular weight of at least $5 \times 10^5$ determined by FPLC (fast protein liquid chromatography) in accordance with the technique disclosed in copending U.S. patent application Ser. No. 816,548 filed Jan. 6, 1986. Average molecular weights in excess of about $1.0 \times 10^6$ preferably $1.2 \times 10^6$, and especially in excess of about $1.8 \times 10^6$ are particularly preferred. It is further preferred that the hyaluronic acid display a fairly narrow molecular weight distribution and a distribution with a single gel permeation peak is particularly preferred. A single symmetrical FPLC peak with 98% of the molecules having a weight between about $1.2 \times 10^6$ and $4.0 \times 10^6$ is especially preferred.

The hyaluronic acid may have either a high or a low viscosity depending on what is convenient for the route of treatment desired. The higher viscosities are convenient for topical applications while the lower viscosities are convenient for the injection routes of administration, i.e. intra-muscular, intravenous or subcutaneous. The higher molecular weight hyaluronic acid may advantageously have viscosities between about 900 and 5000 centistokes per second (c/s) at 37° C. for topical applications and advantageously have viscosities less than about 500, preferably less than 150 c/s at 37° C. for other routes of administration. In both cases the viscosity is conveniently measured as a 1 wt. % aqueous solution of the sodium salt in a Cannon-Manning Semi-Micro Viscometer according to the procedures in ASTM D 445 and D 2515. The low viscosity material greatly facilitates the injection routes of administration by allowing for instance the use of reasonably concentrated aqueous sodium hyaluronate solution in practical size doses. Thus, a 1% aqueous solution of sodium hyaluronate can be readily utilized for injection doses of about 10 milliliters which contain about 100 milligrams of active ingredient if its viscosity is less than about 200 c/s at 37° C.

The treatment of irritated or inflamed mammalian tissue by remote administration requires a dose or total dose regimen effective to reduce or alleviate the trauma. It is preferred to administer at least about 0.02 milligrams of hyaluronic acid per pound of body weight of the mammal being treated which is equivalent to about 0.044 milligrams per kilogram. It is particularly preferred to utilize at least about 0.04 and especially 0.08 milligrams per pound of body weight. In the case of topical application it is particularly desirable to use in excess of about 0.10, especially about 0.15, milligrams per pound of body weight. In as much as hyaluronic acid is a naturally occurring substance in mammals it is believed that there is no inherent upper limit to the tolerable dose. However, as in all medicinal treatments, it is prudent to use no more than is necessary to achieve the desired effect. Furthermore, any impurities which are at a low enough level to be well tolerated at effective dosages may provoke adverse reactions at unwarrentedly high dosages.

The topical treatment should be made by application of the hyaluronic acid combined with a compatible transdermal carrier. Any recognized carrier such as methyl salicylate, sodium salicylate, benzyl alcohol, oleic acid, 10% propylene glycol, 1% sodium glycolate, 1% polyoxyethylene-10-cetyl ether, 0.1% sodium EDTA, 1% sodium dodecyl sulfate, or dimethyl sulfoxide (DMSO) is suitable with DMSO being particularly preferred. A convenient application formulation is a mixture of a less than about 3 weight percent aqueous solution of hyaluronic acid, particularly as sodium hyaluronate, with an effective amount of transdermal carrier. A preferred formulation involves an aqueous between about 0.5 and 2.5 weight percent hyaluronate solution and up to about 30 volume percent of transdermal carrier. The hyaluronate solution and the total formulation both conveniently display a viscosity in excess of about 1000 c/s at 37° C.

The present treatment has been found to be particularly effective in the treatment of joint distress in large mammals including that caused by arthritic conditions. Especially preferred applications involve the treatment of horses and man by intramuscular injection and topical administration in a transdermal carrier. A particularly effective treatment for joint pain in the leg joints, particularly the carpal and tibiotarsal (or hock) joints, of horses is an intramuscular injection preferably in the neck muscle. A particularly effective treatment for musculoskeletal pain in man is topical application in a transdermal carrier such as dimethyl sulfoxide (DMSO). The application may be in the vicinity of the affected joint tissue or it may be considerably more remote.

The remote application techniques of the present invention can also be utilized to alleviate any other condition against which hyaluronic acid is recognized as effective. Among these are the reduction or prevention of adhesions at the site of surgical intrusion, especially in the case of surgery involving tendons.

The remote application techniques of the present invention are of particular interest with regard to those mammals which are among the commonly recognized companions to man. The amelioration of pain or discomfort in these companion animals is of the greatest interest and is the most practical among all treatable mammals. Of particular interest in this group are the cat, dog and horse.

The invention is further illustrated but is not intended to be limited by the following examples.

EXAMPLE 1

An investigation of the intramuscular treatment of horses.

A study involving eight mixed breed female and gelding horses was undertaken to determine if the intramuscular injection of sodium hyaluronate could alleviate the symptoms induced by the intra-articular injection of Freund's Complete Adjuvant into the intercarpal joint. This is a common and well accepted model for the study of joint distress, particularly arthritic conditions, in horses. The study established that three intramuscular injections of 0.08 milligrams per pound of horse weight given in the neck muscle 5, 9 and 13 days after inducement of joint distress with a 0.7 milliliter injection of the Adjuvant was effective.

The eight horses were initially acclimated to the housing facilities and testing apparatus for several days and then evaluated against the test criteria of joint circumference, range of motion, stride and lameness to provide a base score. The following day all eight horses were given a 0.7 milliliter injection of Freund's Complete Adjuvant in the left intercarpal joint. The horses displayed soreness in the left front leg over the next four days. On the fourth day after the intra-articular injection of the irritant the horses were re-rated against the same four criteria. A total score was developed for each horse consisting of the sum of the differences in each parameter except stride between the two measurements. These scores were then used to assign four horses to a control group and four to a treatment group by assigning the horse with the highest score to one group, the horses with the next two highest scores to the other group, the horses with the next two highest scores to the first group, the two horses with the next score to the second group and the last horse to the first group. The first group was designated the control group by an arbitrary toss of a coin. The table of measurements was as follows with measurement days arbitrarily designated −6 and −1:

| Horse No. | Circumference −6 | −1 | Diff. | Range of Motion −6 | −1 | Diff. | Lameness −6 | −1 | Diff. | Total | Stride −6 | −1 | Diff. | Total |
|---|---|---|---|---|---|---|---|---|---|---|---|---|---|---|
| 1 | 31.9 | 36.2 | 4.3 | 155° | 65° | 90° | 0 | 4 | 4 | 98.3 | 157.1 | 138.5 | 18.2 | 116.5 |
| 2 | 29.4 | 34.4 | 5.0 | 150° | 55° | 95° | 0 | 5 | 5 | 105.0 | 161.5 | 76.1 | 85.4 | 190.4 |
| 3 | 29.3 | 33.5 | 3.7 | 160° | 30° | 130° | 0 | 5 | 5 | 138.7 | 151.1 | 78.5 | 82.8 | 221.5 |
| 4 | 30.0 | 35.5 | 5.5 | 195° | 45° | 100° | 0 | 5 | 5 | 110.5 | 160.4 | 0 | 160.4 | 270.9 |
| 5 | 29.3 | 33.4 | 3.6 | 150° | 45° | 105° | 0 | 4 | 4 | 112.6 | 163.1 | 126.7 | 36.4 | 149.0 |
| 6 | 31.5 | 36.2 | 4.7 | 190° | 35° | 105° | 0 | 4 | 4 | 113.7 | 161.3 | 145.7 | 15.6 | 134.2 |
| 7 | 30.5 | 36.0 | 5.5 | 150° | 55° | 95° | 0 | 5 | 5 | 105.5 | 145.4 | 100.9 | 44.5 | 150.0 |
| 8 | 31.0 | 34.5 | 3.5 | 150° | 60° | 90° | 0 | 5 | 5 | 98.5 | 157.9 | 114.7 | 40.2 | 138.7 |

| Ranking | Horse No. |  | Group I | Control | Group II | Treatment |
|---|---|---|---|---|---|---|
| 1 | 3 | 138.7 | 3 | 138.7 | 6 | 113.7 |
| 2 | 6 | 113.7 | 4 | 110.5 | 5 | 112.6 |
| 3 | 5 | 112.6 | 7 | 105.5 | 2 | 105.0 |
| 4 | 4 | 110.5 | 1 | 98.3 | 8 | 98.5 |
| 5 | 7 | 105.0 | Mean Score | 113.25 | Mean Score | 107.45 |
| 6 | 2 | 105.0 |  |  |  |  |
| 7 | 8 | 98.5 |  |  |  |  |
| 8 | 1 | 98.3 |  |  |  |  |

On the next day (day 0) each of the horses was given an injection in the neck muscle of between 7.5 and 9.5 milliliters, depending on body weight. Each horse received an injection to the nearest 0.5 ml of 0.008 milliliters per pound of weight. The injection for the treatment horses consisted of a sterile 1.19 wt. % aqueous solution of sodium hyaluronate having a FPLC determined average molecular weight of $1.88 \times 10^6$, a nucleic acid content of less than 0.003 mg/ml by ethidium bromide fluoresence, a total amino acid content by orthophthalaldehyde fluoresence of less than 0.005 mg/ml and a 37° C. viscosity of 147 c/s while the injection for the control horses consisted of a sterile phosphate buffered saline solution. The weight of each horse and the dosage given to it at this time and four and eight days subsequently was as follows:

| HORSE | WEIGHT IN LBS | DOSE IN ML |
|---|---|---|
| 1 | 1190 | 9.5 |
| 2 | 1015 | 8.0 |
| 3 | 985 | 8.0 |
| 4 | 1215 | 9.5 |
| 5 | 1030 | 8.0 |
| 6 | 1210 | 9.5 |
| 7 | 945 | 7.5 |
| 8 | 1180 | 9.5 |

The injection site was palpated and the body temperature was taken daily for three days after the first injection and at the time of the second and third injections and finally four days after the third injection. The IM treatment produced no deleterious effect. All temperatures remained normal and there was no clinically significant injection site reaction (the Freund's Complete Adjuvant is a "known pyrogen" so temperature normality was judged by the fact that the treatment injections did not cause any further temperature elevation and did not appear to interfere with the drop in temperature from the peak induced by the traumatizing injection).

Each horse was evaluated against the criteria of joint circumference, range of motion, stride length and observed lameness seven, fourteen, twenty-one, twenty-eight, thirty-five and forty-two days after the first injection. These were the same parameters as had been used to classify the horses into the treatment and control groups and were defined as follows:

Joint Evaluation Procedure

1. Joint Circumference

Joint circumference was measured while at the stall before exercise. It was measured at a point directly over the accessory carpal bone. It was measured with a cloth tape and recorded in centimeters.

2. Range of Motion

Range of Motion was measured at the stall. It was the difference between the angle of the affected leg at rest and the flexed angle. All three values were recorded. A goniometer was used to determine the angles.

a. Leg at rest: With the horse in a standing position, the goniometer measured the angle of the carpus.

b. Flexed angle: The affected joint was flexed while the leg was raised from the ground. The goniometer measured the angle at the point where the horse reacted to the flexion by flinching, shying or pulling back.

3. Stride Length

Stride length was measured before being placed on the walker. A long paper roll (20 feet) was used to record the distance between toe marks. Prior to walking across the paper, the toe of the affected leg was sloshed with water or mineral oil. Two steps were recorded and the distance between the toe mark from the affected leg was measured in centimeters. The horse was walked across the paper three times. An average of the three measurements was used for the final value.

the "day" is the days before or after the first injection:

|  | Horse No. | Parameter | Day −6 | −1 | 7 | 14 | 21 | 28 | 35 | 42 |
|---|---|---|---|---|---|---|---|---|---|---|
| Treatment | 8 | Circum. | 31.0 | 34.5 | 36.4 | 36.7 | 36.1 | 35.6 | 35.2 | 35.8 |
|  | 2 | (in. cm) | 29.4 | 34.5 | 33.5 | 34.5 | 34.6 | 33.8 | 34.2 | 34.0 |
|  | 5 |  | 29.8 | 33.4 | 37.2 | 36.3 | 37.7 | 35.5 | 36.2 | 35.5 |
|  | 6 |  | 31.5 | 36.2 | 36.6 | 35.5 | 35.8 | 34.0 | 35.3 | 34.5 |
| Control | 3 |  | 29.8 | 33.5 | 35.7 | 36.8 | 36.8 | 37.2 | 36.3 | 39.3 |
|  | 4 |  | 30.0 | 35.5 | 35.5 | 36.4 | 36.3 | 35.3 | 36.5 | 34.0 |
|  | 1 |  | 31.9 | 36.2 | 37.0 | 36.8 | 37.5 | 37.5 | 39.4 | 38.8 |
|  | 7 |  | 30.5 | 36.0 | 36.6 | 36.8 | 37.7 | 36.4 | 39.2 | 40.0 |
| Treatment | 8 | Range of | 150° | 60° | 40° | 70° | 95° | 100° | 100° | 95° |
|  | 2 | Motion | 150° | 55° | 75° | 95° | 95° | 110° | 95° | 100° |
|  | 5 |  | 150° | 45° | 65° | 70° | 70° | 70° | 75° | 70° |
|  | 6 |  | 140° | 35° | 85° | 115° | 130° | 110° | 115° | 105° |
| Control | 3 |  | 160° | 30° | 50° | 45° | 40° | 55° | 75° | 55° |
|  | 4 |  | 145° | 45° | 50° | 55° | 60° | 80° | 75° | 85° |
|  | 1 |  | 155° | 65° | 85° | 75° | 95° | 90° | 75° | 75° |
|  | 7 |  | 150° | 55° | 85° | 85° | 55° | 75° | 75° | 55° |
| Treatment | 8 | Lameness | 0 | 5 | 4 | 1 | 0 | 1 | 0 | 0 |
|  | 2 |  | 0 | 5 | 3 | 1 | 1 | 1 | 0 | 0 |
|  | 5 |  | 0 | 4 | 4 | 3 | 3 | 2 | 0 | 0 |
|  | 6 |  | 0 | 4 | 1 | 0 | 0 | 0 | 0 | 0 |
| Control | 3 |  | 0 | 5 | 4 | 4 | 4 | 4 | 4 | 4 |
|  | 4 |  | 0 | 5 | 5 | 4 | 4 | 3 | 1 | 1 |
|  | 1 |  | 0 | 4 | 4 | 2 | 4 | 4 | 3 | 1 |
|  | 7 |  | 0 | 5 | 4 | 4 | 4 | 4 | 3 | 3 |
| Treatment | 8 | Stride | 154.9 | 114.7 | 136.7 | 148.2 | 144.9 | 149.0 | 149.5 | 154.0 |
|  | 2 | (in inches) | 161.5 | 76.1 | 148.8 | 155.0 | 145.3 | 157.4 | 156.8 | 162.6 |
|  | 5 |  | 163.1 | 126.7 | 135.8 | 156.9 | 153.4 | 155.4 | 159.8 | 169.3 |
|  | 6 |  | 161.3 | 145.7 | 149.2 | 161.8 | 168.2 | 164.7 | 165.2 | 167.1 |
| Control | 3 |  | 157.3 | 74.5 | 106.5 | 123.6 | 128.5 | 130.0 | 111.2 | 128.2 |
|  | 4 |  | 160.4 | 0* | 108.9 | 142.9 | 143.7 | 152.1 | 147.1 | 151.7 |
|  | 1 |  | 157.7 | 139.5 | 145.2 | 163.8 | 160.7 | 152.0 | 164.9 | 165.0 |
|  | 7 |  | 145.4 | 100.9 | 142.5 | 133.3 | 144.9 | 139.3 | 159.0 | 145.9 |

*A zero indicates that the horse did not put the affected foot to the paper thus no stride could be measured.

4. Observed Lameness

The horse was placed on the mechanical walker and walked at 6 m.p.h. for five minutes. The score is determined while on the walker. The direction of the mechanical walker was such that the affected leg was to the inside.

- 0=No Lameness
- 1=Difficult to observe; not consistently apparent regardless of circumstances (i.e., weight-carrying, circling, inclines, hard surface, etc.).
- 2=Difficult to observe at a walk or trotting a straight line; consistently apparent under certain circumstances (i.e., weight-carrying circling, inclines, hard surface, etc.).
- 3=Consistently observable at a trot under all circumstances.
- 4=Obvious lameness; marked nodding, hitching or shortened stride.
- 5=Minimal weight-bearing in motion and/or at rest: inability to move.

If a horse was very reluctant to move, and placement on the mechanical walker was not advised, a score of 5 was recorded and the horse was returned to the stall.

An analysis of these parameters clearly demonstrated the beneficial result of the intramuscular injections of the hyaluronic acid in relieving the trauma induced by the Freund's Complete Adjuvant. The treatment horses displayed clearly superior performance to the control horses in every parameter but joint circumference for which the results were not as conclusive. This is in accord with other studies on the relief of trauma in horse joints wherein joint circumference was found not to be a particularly sensitive measurement parameter. The results are tabulated in the following table in which Analyses of these results were plotted for each parameter along with some data on the intra-articualr treatment of horse joints similarly traumatized by the injection of Freund's Complete Adjuvant. However, the induced trauma was somewhat less severe than that of the present study so the control horses from this study had a range of motion not too different than the treatment horses of the present study. But, more importantly, the difference in recovery of range of motion and lameness between treatment and control horses for the present study closely paralleled that observed in the earlier study. Thus, the effects obtained by intramuscular injection were highly similar to those previously obtained by intra-articular administration.

These analyses are displayed in FIGS. 1 through 6. In these figures the open squares represent the average values for the four treatment horses and the open triangles represent the average values for the four control horses of this study. The hexagons and shaded squares represent the average values for horses with a similarly induced joint trauma who were treated intra-articularly with a single dose of 40 and 20 milligrams, respectively, of a similar aqueous sodium hyaluronate solution while the shaded triangles represent the average values for the untreated control horses used in this earlier study.

Figure 1:
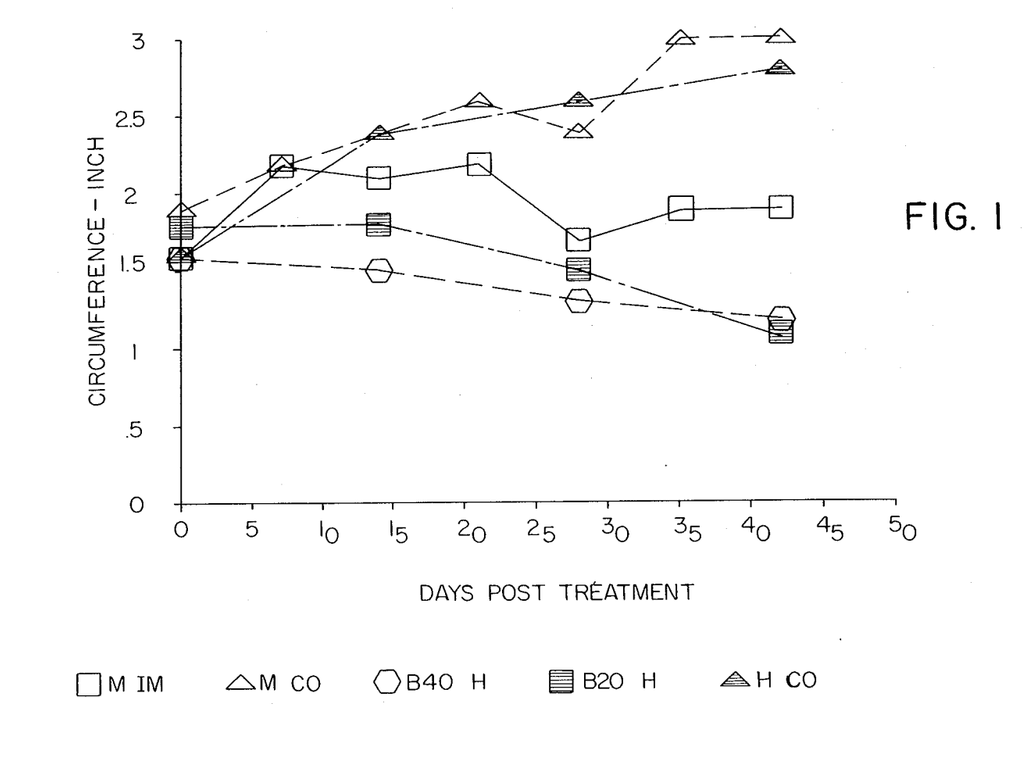
FIG. 1 is a set of plots of the change in carpal joint circumference versus the time after treatment with hyaluronic acid for treated and control horses with Freund's Complete Adjuvant induced trauma in the carpal joint.

FIG. 1 displays the change in the "joint circumference" from the day before the first injection until the end of the study forty three days later (for convenience the "day -1" value has been plotted on the 0 axis and represents the increase in joint circumference (in inches) since the day before the traumatizing injection, i.e. day −6). Although the joint swelling is never completely reversed, it is stabilized at a lower level or partially alleviated by hyaluronic acid treatment. The effect is somewhat less dramatic with the present (intramuscular) route of administration but is clearly present and is on joints which were indicated by the other parameters to be more severely traumatized than those treated intra-articularly.

Figure 2:
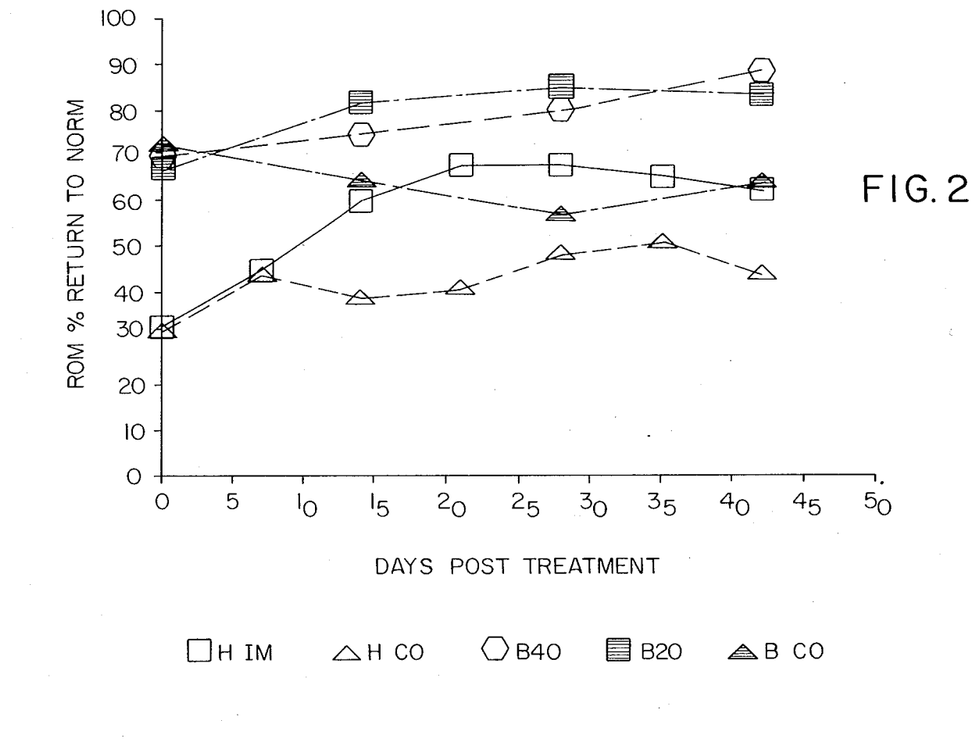
FIG. 2 is a set of plots of the change in range of motion versus the time after treatment for the same horses as in FIG. 1.

FIG. 2 displays the change in the "range of motion" (ROM) over the same time period as FIG. 1. The 100% value is based on the ROM displayed the day before traumatization, i.e. on day −6. It is clear that the joints evaluated in the comparison intra-articular study were less traumatized because the inhibition of the ROM before treatment was less severe.

It is also clear that the intramuscular and the intra-articular treatments have caused parallel improvements over their respective controls. However, because the Freund's Complete Adjuvant causes an extreme trauma neither the inventive or the comparison treatment could completely alleviate the induced condition.

Figure 3:
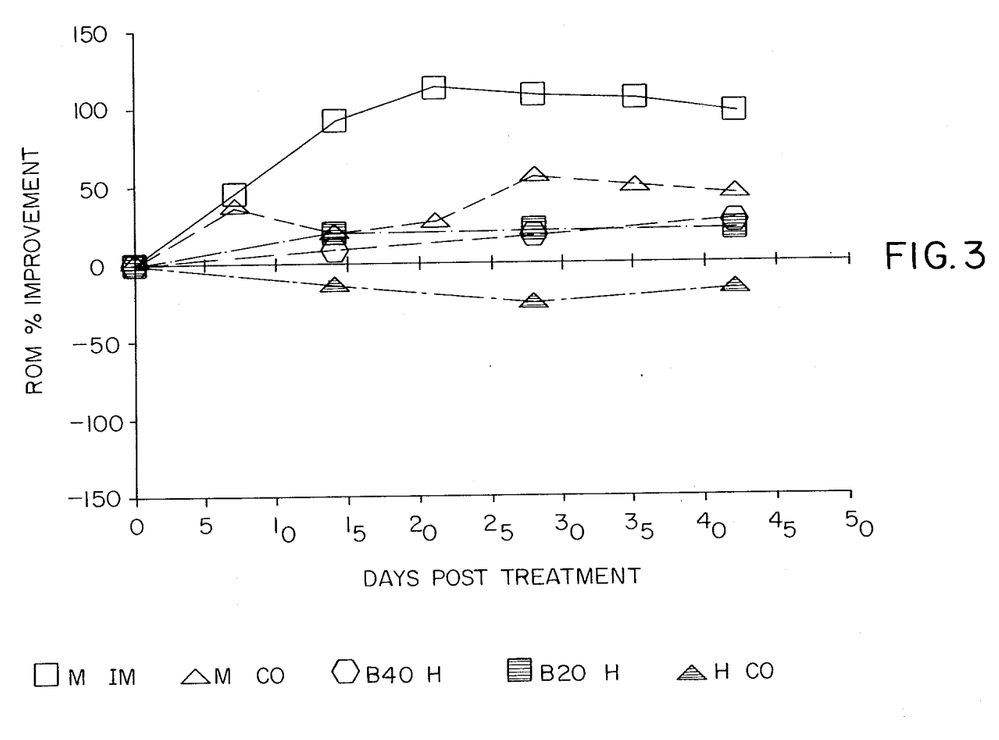
FIG. 3 is a set of plots of the change in range on motion normalized to the day of treatment versus the time after treatment for the same horses as in FIG. 1.
Figure 4:
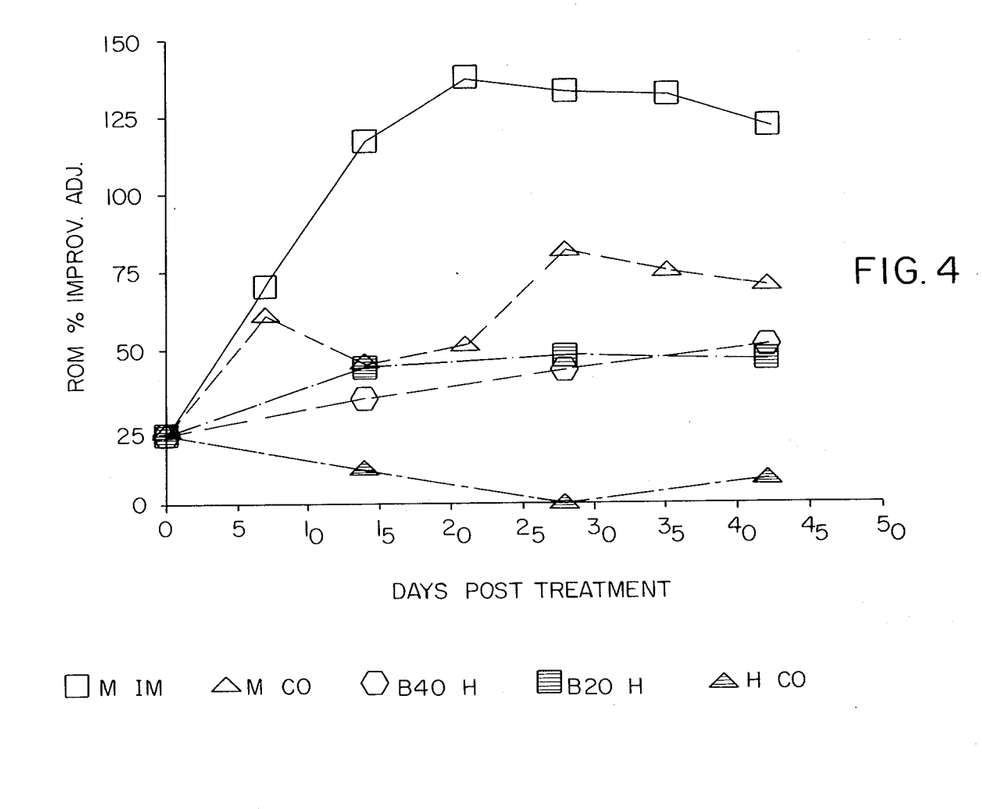
FIG. 4 is the same set of plots as in FIG. 3 but with all ordinate values arbitrarily increased by 23.7% to set the lowest point at 0%.

FIGS. 3 and 4 display further analyses of the ROM data wherein the percent of improvement over the condition the day before the first treatment injection is evaluated. The time scale is the same as in FIGS. 1 and 2. In FIG. 4 the graph has been arbitrarily adjusted upward by adding 23.7% to all ordinate values. Here it appears that the present invention's intramuscular administration results in a greater improvement over its control than in the case of the intra-articular administration.

Figure 5:
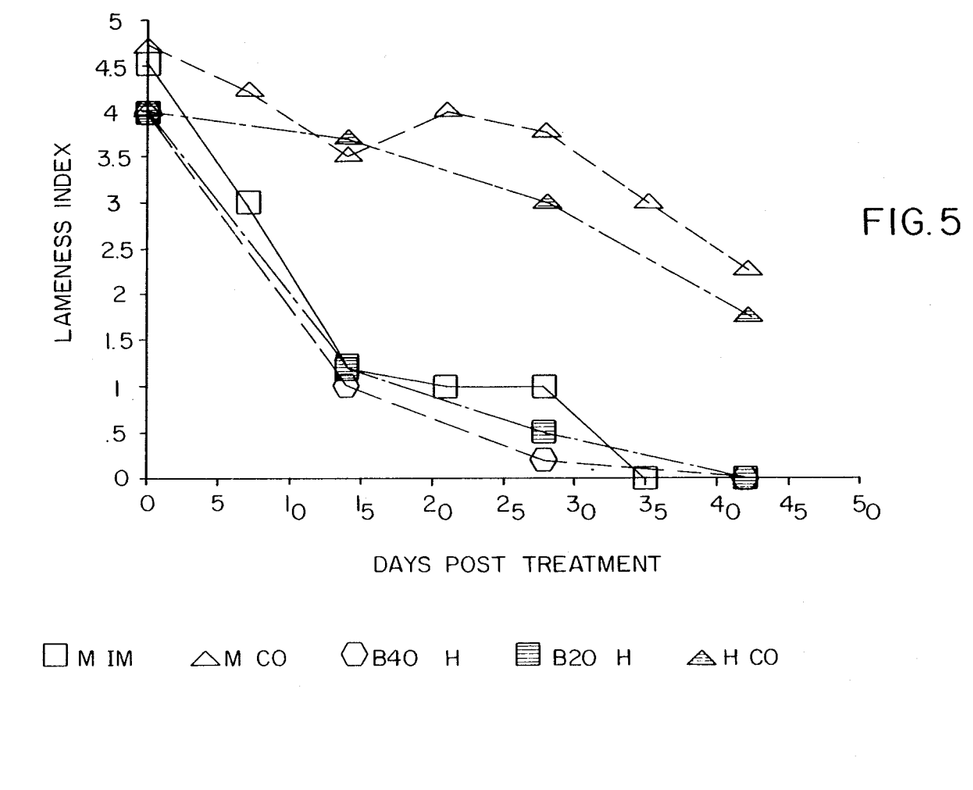
FIG. 5 is a set of plots of lameness index versus time after treatment for the same horses as in FIG. 1.

FIG. 5 displays the change of the "observed lameness" over the same period as the previous figures. The intramuscular and the intra-articular routes of administration displayed approximately equivalent effects. The controls for the present study showed a somewhat higher degree of lameness suggesting that the traumatization for the present study was somewhat more severe than for the prior intra-articular study. The fact that the same level of lameness was obtained from both routes of administration suggests the route of the present invention might be somewhat more effective.

Figure 6:
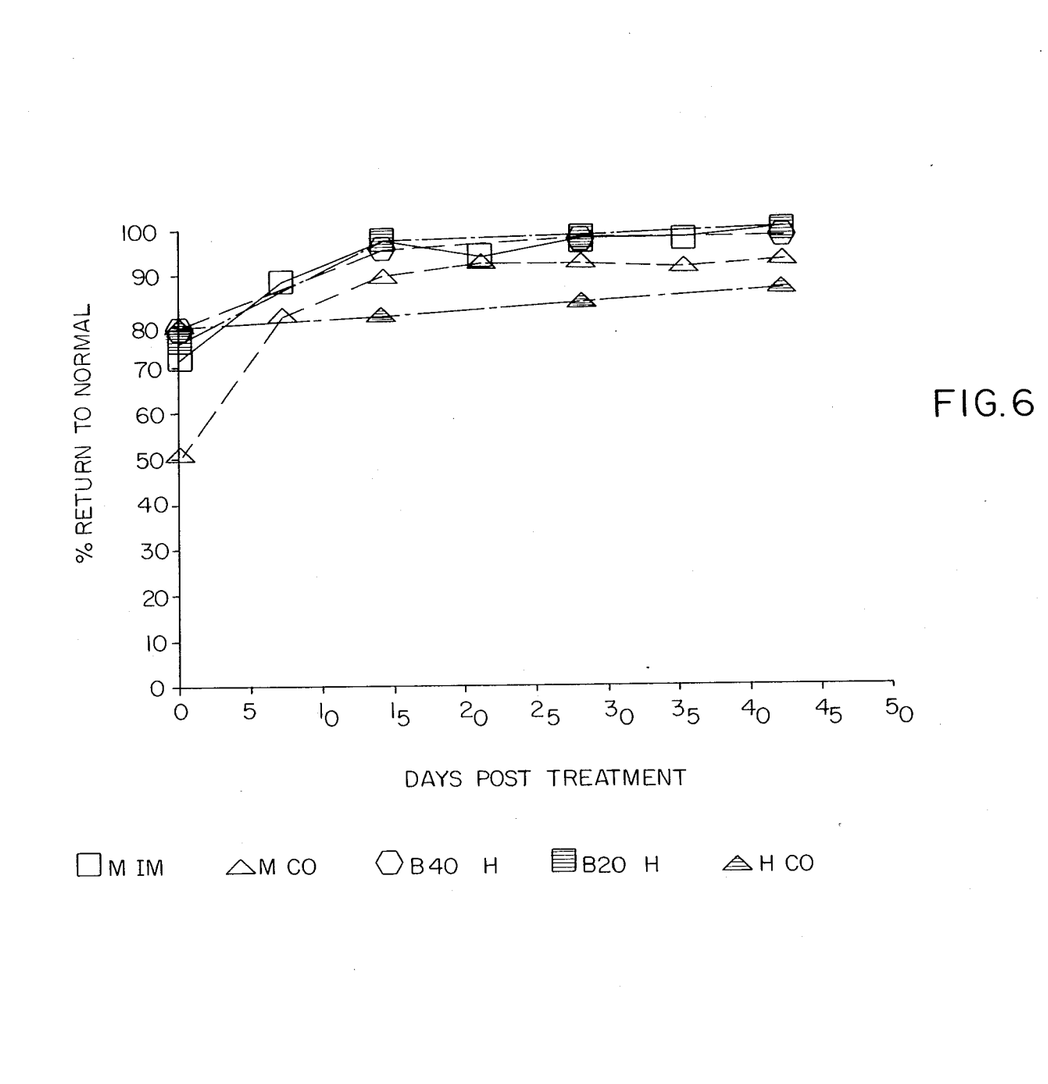
FIG. 6 is a set of plots of the per cent improvement in stride versus time after treatment for the same horses as in FIG. 1.

FIG. 6 displays the change in "stride length" over the same time period as the previous Figures. The stride at each evaluation was compared to the average value displayed the day before the traumatizing injection, i.e. day −6, to obtain a percentage of recovery. The horses treated according to both the present invention and intra-articular injection show a faster and greater ultimate recovery of stride compared to their respective controls.

EXAMPLE 2

Back pain in a man aged 48, weight 155 pounds was alleviated by topical application of an aqueous solution of sodium hyaluronate mixed with 10 to 30 volume per cent of dimethyl sulfoxide (DMSO). In particular preparations were made up with 10, 20 and 30 volume per cent of DMSO and the balance a 1.7 weight per cent solution of sodium hyaluronate with a 37° C. viscosity of in excess of 500 c/s and a FPLC determined molecular weight of $2 \times 10^6$ daltons with a nucleic acid content of 0.00137 mg/ml and a total amino acid content by orthophthalaldehyde fluorescence of 0.0047 mg/ml. Applications of about 2 ml of preparation were made to the back in the vicinity of the pain twice daily for a period of two weeks. In each case the pain was relieved in about 15 minutes and the relief lasted about 8 to 10 hours. Treatment was then suspended and the pain returned in about four to five days. At this time treatment was resumed by the daily application of about 2 ml of the preparation to the knuckles of the hands with effective relief of the pain. This treatment was discontinued after three days and the pain did not reoccur in the next two and a half weeks. Thus, the pain was effectively treated with a topical dose of about 0.15 milligrams per pound of body weight (2 ml×1.7 wt. %×70 vol. %×1000 mg/ml) applied either in the vicinity of the pain or at a more remote location.

The pain relieved by this treatment had been close to constant for about two years before treatment was initiated. After treatment the pain was observed at a much lower intensity only after sitting or sleeping in a constant position for a prolonged period.

The topical application of the sodium hyaluronate without a transdermal carrier was ineffective. The hyaluronate solution simply evaporated to dryness leaving a film on the skin of the subject.

The application of equivalent amounts of DMSO alone was ineffective to relieve the back pain. In fact, it caused some irritation of the skin area to which it was applied. This was in distinct contrast to the application in combination with the sodium hyaluronate solution in which no skin irritation was observed.

EXAMPLE 3

Various joint and muscle pains were relieved in a man age 54 weighing 250 pounds by the topical application of the same aqueous sodium hyaluronate used in Example 2 combined with 20 volume per cent of DMSO, based on total volume. A knee causing pain from several year old cartilage damage was treated with 4 milliliters of this preparation and relief was observed within 30 minutes. Treatment was repeated on four day intervals to successfully control the pain for about two weeks. Bursitis pain in a shoulder was successfully alleviated within a few minutes on the topical application of about 5 ml of this same preparation. Pain returned in about four days and was relieved by the same treatment. The cycle was repeated four times. Pain from sore muscles in the clavicle region was relieved by the application of 3 milliliters of this preparation. Application was made to one side only and pain persisted in the untreated side.

EXAMPLE 4

A severe back pain in a man age 57 weighing 195 lbs. who had multiple prolapsed disc in the lumbar area causing muscle spasms was relieved by the topical application of 2 milliliters of the preparation described in Example 2 with 20 volume per cent DMSO. The preparation was applied to the skin over the lumbar spine and relieved the pain within one hour for approximately eight hours. The treatments were continued on twelve hour intervals for a period of several days with an occasionally skipped treatment. On some occassions the treatment was not effective but in such cases the subsequent treatment was effective.

The condition being treated had been treated by enzyme injection therapy more than a year previously. Elective surgery was being considered at the time the present treatment was initiated.

EXAMPLE 5

Two quarter horses, normally actively engaged in barrel racing, developed tendonitis of the flexor tendons of both hind legs and were successfully treated by topical application of the aqueous sodium hyaluronate solution of Example 2 mixed with a transdermal carrier. The 80 volume percent hyaluronate/20 volume percent dimethyl sulfoxide mixture was more effective than a commercially available topical agent, Absorbine. One leg of each horse was treated with hyaluronate mixture and the other was treated with the Absorbine. The hyaluronate was applied twice each day for three days using three milliliter applications the first day and one milliliter application the subsequent two days (in each case ½ of each application was applied on each side of the leg). At the end of three days the symptons, swelling over the tendon and sheath and soreness over the sesamoid bones, were eliminated. The primary lesion was gone. On the other hand, treatment with Absorbine in the recommended manner required six days of treatment for complete relief.

COMPARATIVE EXAMPLE 1

Two experiments were conducted which demonstrated a limitation in the remote administration of hyaluronic acid. Two of the control horses from the study reported in Example 1 were treated topically and two others were treated intravenously after their joint traumas had become chronic and no significant improvement in their conditions was observed. Although some relief of a chronic condition induced by Freund's Complete Adjuvant has been reported for the intra-articular injection of sodium hyaluronate in European Published Patent Application 144,019 this model is commonly restricted to the evaluation of the treatment of acute conditions. The lesions developed an extended period after traumatization are so severe that they are not normally expected to respond to treatment. Thus, these results are not judged to be a major limitation on remote administration and may, in fact, only be reflective of the severity of the induced trauma.

The topical treatment was given on a daily basis for six days beginning on "day 28" of the Example 1 study, i.e. thirty-four days after the induction of trauma, by the application of ten milliliters of a 80 volume percent hyaluronate solution/20 volume percent dimethyl sulfoxide mixture to the affected joint. The aqueous hyaluronate solution was the same as utilized in Example 2. No significant improvement in any of the four criteria of Example 1 were observed as compared to either the immediate pretreatment condition or the other two control horses.

The intravenous treatment was given every other day for eight days beginning on "day 35" of the Example 1 study, i.e. forty-one days after the induction of trauma, by injection into the jugular vein of four milliliters of the aqueous sodium hyaluronate solution used in Example 1. Once again no significant improvement in any of the four criteria was observed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for reducing the inflamation, pain or other result of trauma in irritated mammalian tissue comprising administering an effective dose of hyaluronic acid or a pharmacologically acceptable salt thereof at an effective site in or on the body of the mammal remote from said tissue.

2. The process of claim 1 wherein the dose is administered topically, subcutaneously, intramuscularly or intravenously.

3. The process of claim 2 wherein the irritated or inflammed tissue is present in a joint.

4. The process of claim 2 wherein the irritated or inflammed tissue is at the site of a surgical intrusion.

5. The process of claim 4 wherein the irritated or inflammed tissue is at the site of tendon surgery and the treatment reduces the incidence of adhesions.

6. The process of claim 2 wherein the inflamation is a result of an arthritic condition of a joint.

7. The process of claim 2 wherein the inflammation and soreness of a horse joint is at least partially alleviated.

8. The process of claim 7 wherein the dose is at least about 0.02 mg. per pound of body weight of the subject being treated.

9. The process of claim 7 wherein the dose is at least 0.04 mg per pound of body weight of the subject being treated.

10. The process of claim 2 wherein the dose is at least about 0.02 mg. per pound of body weight of the subject being treated.

11. The process of claim 9 wherein the dose is at least 0.08 mg per pound of body weight of the subject being treated.

12. The process of claim 10 wherein the hyaluronic acid is administered by an injection route as an aqueous 0.5 to 3.0 weight per cent solution having a 37° C. viscosity of less than about 200 c/s.

13. The process of claim 10 or 12 wherein the hyaluronic acid has an FPLC determined molecular weight distribution lying almost entirely between 1.5 and 4 million daltons.

14. The process of claim 13 wherein the hyaluronic acid is non-pyrogenic and by UV absorbance has a combined amino acid and protein content of less than about 1.25 mg/ml and a nucleic acid content of less than about 0.06 mg/ml.

15. A process of at least partially alleviating inflammation or soreness or both of a horse joint comprising the intramuscular injection to such horse of an approximately one weight percent aqueous solution of sodium hyaluronate having a 37° C. solution viscosity below about 200 c/s and a FPLC determined molecular weight distribution which is a single significant peak lying between about 1.5 and 4.0 million daltons at a dose of at least about 0.04 mg. of hyaluronate per pound of horse body weight.

16. The process of claim 15 wherein the treatment regimen comprises three injections of at least about 0.04 mg. of sodium hyaluronate each.

17. The process of claim 16 wherein the injections are given at four day intervals.

18. The process of claim 2 wherein the hyaluronic acid is administered topically in combination with a transdermal carrier.

19. The process of claim 18 wherein the 37° C. viscosity of the treatment combination is in excess of about 1000 c/s.

20. The process of claim 18 wherein the transdermal carrier is selected from the group consisting of methyl salicylate, sodium salicylate, benzyl alcohol, oleic acid, 10% propylene glycol, 1% sodium glycolate, 1% polyoxyethylene-10-cetylether, 0.1% sodium EDTA, 1% sodium dodecyl sulfate and dimethyl sulfoxide.

21. The process of claim 20 wherein the transdermal carrier is dimethyl sulfoxide.

22. The process of claim 18 wherein the hyaluronic acid is between about 0.5 and 3.0 weight percent aqueous solution and is mixed with up to about 30 volume percent of a transdermal carrier.

23. The process of claim 22 wherein the hyaluronic acid has a FPLC determined molecular weight of at least $5 \times 10^5$ daltons, a combined amino acid and protein content of less than about 1.25 mg/ml by UV absorption and a nucleic acid content of less than about 0.06 mg/ml by UV absorption.

24. The process of claim 23 wherein the hyaluronic acid has a FPLC determined molecular weight distribution 98% of which lies in a single symetrical peak between about 1.5 and $4.0 \times 10^6$ daltons.

25. The process of claim 24 wherein the hyaluronic acid is in the form of its sodium hyaluronate salt.

26. The process of claim 18 wherein the dose is in excess of about 0.10 milligrams per pound of body weight of the mammal being treated.

27. A process of relieving joint or muscle pain in a mammal comprising the topical application to such mammal, at an effective site of a mixture of between about 0.5 and 2.5 weight percent of a non-pyrogenic aqueous sodium hyaluronate solution having a UV absorbance determined combined amino acid and protein content of less than 1.25 mg/ml, a UV absorbance determined nucleic acid content of less than about 0.06 mg/ml, and a FPLC determined average molecular weight of greater than about $5 \times 10^5$ daltons and up to about 30 volume percent, based on the volume of the mixture, of a transdermal carrier at a dosage of greater than about 0.10 mg per pound of body weight of the mammal being treated.

28. The process of claim 27 wherein the transdermal carrier is selected from the group consisting of methyl salicylate, sodium salicylate, benzyl alcohol, oleic acid, 10% propylene glycol, 1% sodium glycolate, 1% polyoxyethylene-10-cetylether, 0.1% sodium EDTA, 1% sodium dodecyl sulfate and dimethyl sulfoxide.

29. The process of claim 27 wherein the sodium hyaluronate has a UV absorbance determined combined amine acid and protein content of less than about 0.1 mg/ml, a UV absorbance determined nucleic acid content of less than about 0.005 mg/ml and a FPLC determined molecular weight distribution 98% of which lies in a single symmetrical peak between about 1.5 and $4.0 \times 10^6$ daltons.

30. The process of claims 27, 28 or 29 wherein the mammal is man.

31. The process of claims 27, 28 or 29 wherein the mammal is selected from the group consisting of the horse, the dog and the cat.

32. The process of claim 27 wherein the application is made in the vicinity of the origin of the pain.

33. The process of claim 27 wherein the application is made at a site substantially removed from the source of the pain.

34. A process for the at least partial alleviation of arthritic symptons in a mammalian joint comprising the administration to such mammal of an effective dose of hyaluronic acid or a pharmacologically acceptable salt thereof at an effective site in or on the body of the mammal remote from the arthritic joint.

35. A process for reducing the tendency of adhesions to form at the site of a surgical intrusion into a mammalian body comprising the administration to such mammal of an effective dose of hyaluronic acid or a pharmacologically acceptable salt thereof at an effective site on or in the body of the mammal remote from the surgical intrusion.

* * * * *